(12) United States Patent
Randall et al.

(10) Patent No.: US 6,190,590 B1
(45) Date of Patent: Feb. 20, 2001

(54) APPARATUS AND METHOD FOR MAKING FLANGED GRAFT FOR END-TO-SIDE ANASTOMOSIS

(75) Inventors: Scott Randall, Mesa; Roy H. Tang, Phoenix; Albert L. Lamay, Tempe, all of AZ (US)

(73) Assignee: Impra, Inc., Tempe, AZ (US)

( * ) Notice: Under 35 U.S.C. 154(b), the term of this patent shall be extended for 0 days.

(21) Appl. No.: 09/125,910

(22) PCT Filed: Feb. 28, 1996

(86) PCT No.: PCT/US96/02715

§ 371 Date: Aug. 27, 1998

§ 102(e) Date: Aug. 27, 1998

(87) PCT Pub. No.: WO97/31590

PCT Pub. Date: Sep. 4, 1997

(51) Int. Cl.[7] .......................... B29C 33/30; B29C 49/44; B29C 55/24; B29C 69/02; B29D 23/00

(52) U.S. Cl. .......................... 264/138; 264/151; 264/159; 264/296; 264/314; 264/320; 264/523; 264/540; 264/573; 264/536; 264/138; 425/182; 425/185; 425/195; 425/389; 425/392; 425/393; 425/527; 425/531; 623/1; 623/11; 623/12

(58) Field of Search .................................. 264/101, 151, 264/159, 296, 320, 314, 523, 536, 540, 571, 573; 425/185, 195, 392, 393, 387.1, 388, 389, 522, 527, 531, 182; 623/1, 11, 12

(56) References Cited

U.S. PATENT DOCUMENTS

| | | | |
|---|---|---|---|
| 4,234,535 | * | 11/1980 | Okita .................................. 264/519 |
| 4,313,231 | | 2/1982 | Koyamada ............................ 3/1.4 |
| 4,601,718 | * | 7/1986 | Possis et al. ........................ 623/1 |
| 4,714,421 | * | 12/1987 | D'Agostino .................... 425/192 R |
| 4,816,028 | * | 3/1989 | Kapadia et al. ...................... 623/1 |
| 4,840,940 | * | 6/1989 | Scottiurai ........................... 514/56 |
| 4,935,190 | * | 6/1990 | Tennerstedt ........................ 264/529 |
| 4,957,669 | * | 9/1990 | Primm ................................. 264/23 |

(List continued on next page.)

OTHER PUBLICATIONS

Wells et al.; "Effect of carotid artery geometry on the magnitude and distribution of wall shear stress gradients"; Apr. 1996; Journal of Vascular Surgery, vol. 23, No. 4; pp. 667–678.*

Crawshaw et al.; "Flow Disturbance at the Distal End-to--Side Anastomosis"; Nov. 1980; Arch Surg, vol. 115; pp. 1280–1284.*

Dobrin et al.; "Mechanical factors predisposing to intimal hyperplasia and medial thickening in autogenous vein grafts"; Mar. 1989; Surgery, vol. 105, No. 3; pp. 393–400.*

Fillinger et al.; "Beneficial Effects of Banding on Venous Intimal–Medial Hyperplasia in Arteriovenous Loop Grafts"; Aug. 1989; The American Journal of Surgery, vol. 158; pp. 87–94.*

Fillinger et al.; "Graft Geometry and Venous Intimal–Medial Hyperplasia in Arteriovenous Loop Grafts"; Apr. 1990; Journal of Vascular Surgery, vol. 11, No. 4; pp. 556–566.*

*Primary Examiner*—Jan H. Silbaugh
*Assistant Examiner*—Michael I. Poe
(74) *Attorney, Agent, or Firm*—Morrison & Foerster LLP; Todd W. Wight

(57) ABSTRACT

A method and apparatus for forming a flanged polytetrafluoroethylene cuffed section from a tubular polytetrafluoroethylene graft. The flanged polytetrafluoroethylene graft is well suited for use as a distal bypass graft, for arteriovenous grafting, or as a hemodialysis access graft. The graft includes an integral terminal polytetrafluoroethylene flanged skirt or cuff section which facilitates an end-to-side anastomosis directly between an artery and the polytetrafluoroethylene flanged graft without need for an intervening venous collar or venous patch.

19 Claims, 4 Drawing Sheets

U.S. PATENT DOCUMENTS

| | | | |
|---|---|---|---|
| 5,100,422 | 3/1992 | Berguer et al. | 606/151 |
| 5,156,619 | 10/1992 | Ehrenfeld | 623/1 |
| 5,304,340 * | 4/1994 | Downey | 264/521 |
| 5,752,934 * | 5/1998 | Campbell et al. | 604/96 |
| 5,843,158 * | 12/1998 | Lenker et al. | 623/1 |
| 6,019,788 * | 2/2000 | Butters et al. | 623/1 |

* cited by examiner

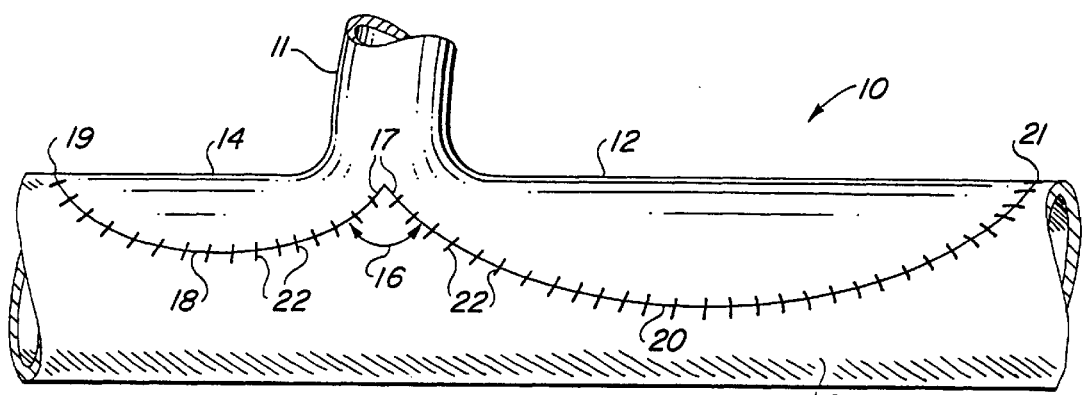
FIG-4A
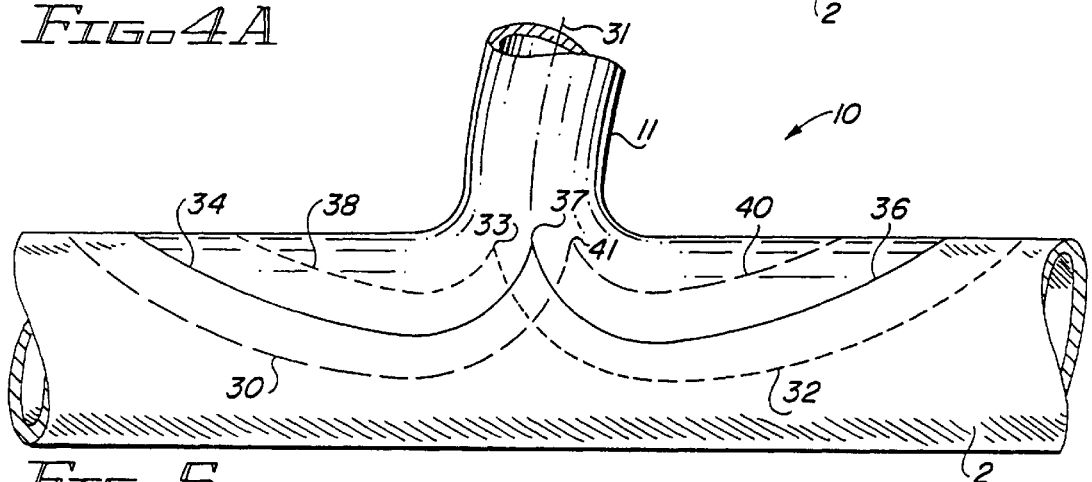
FIG-5
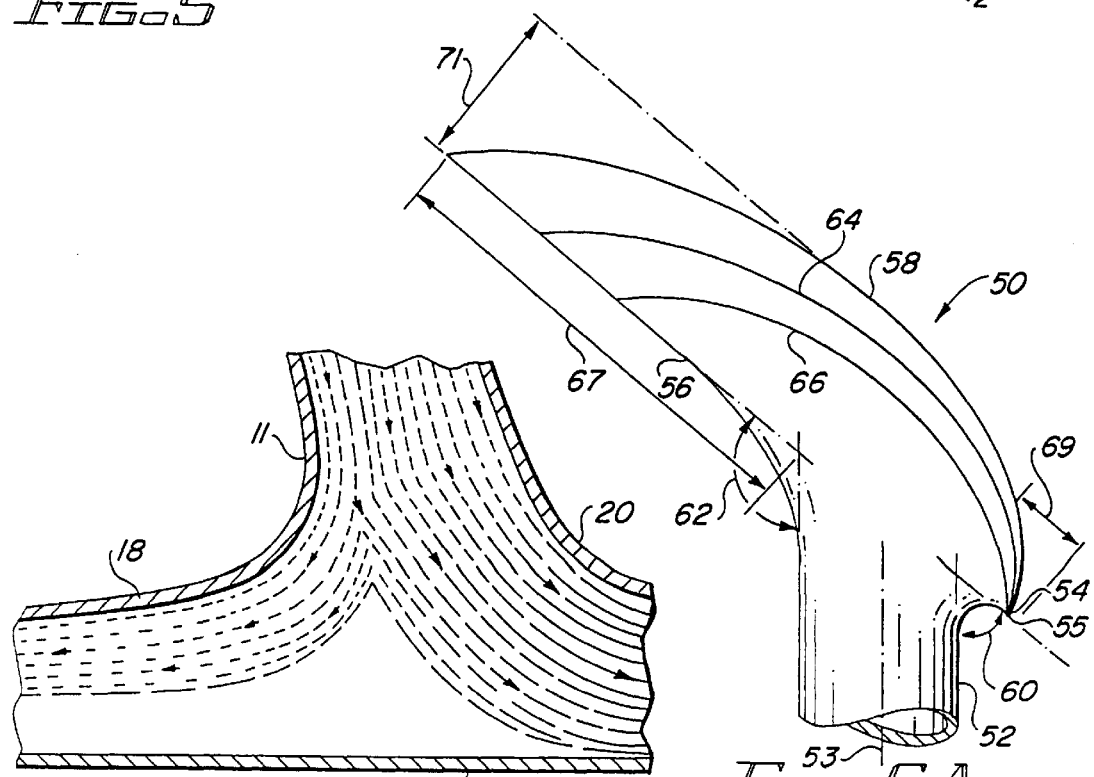
FIG-7
FIG-6A

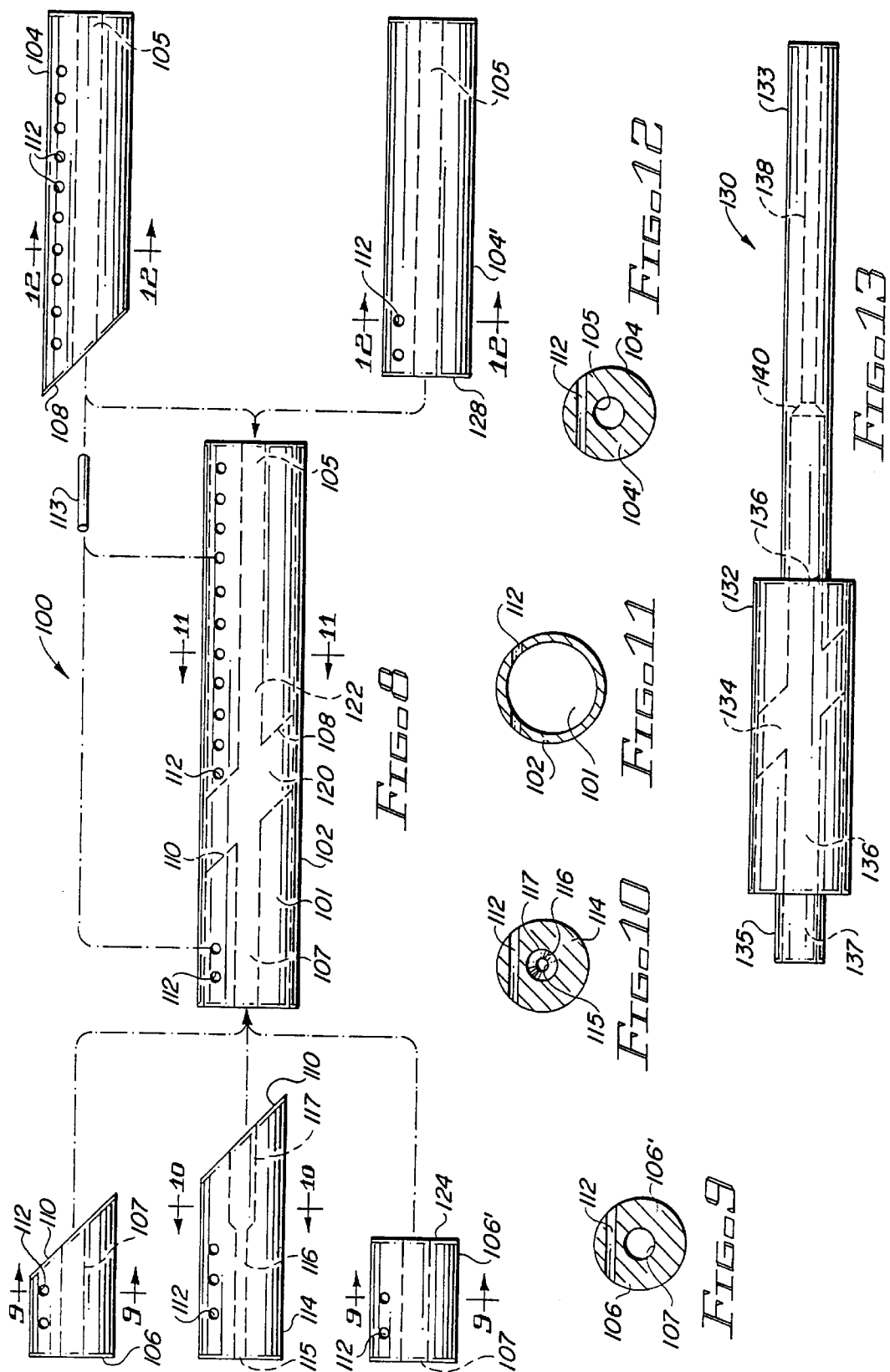

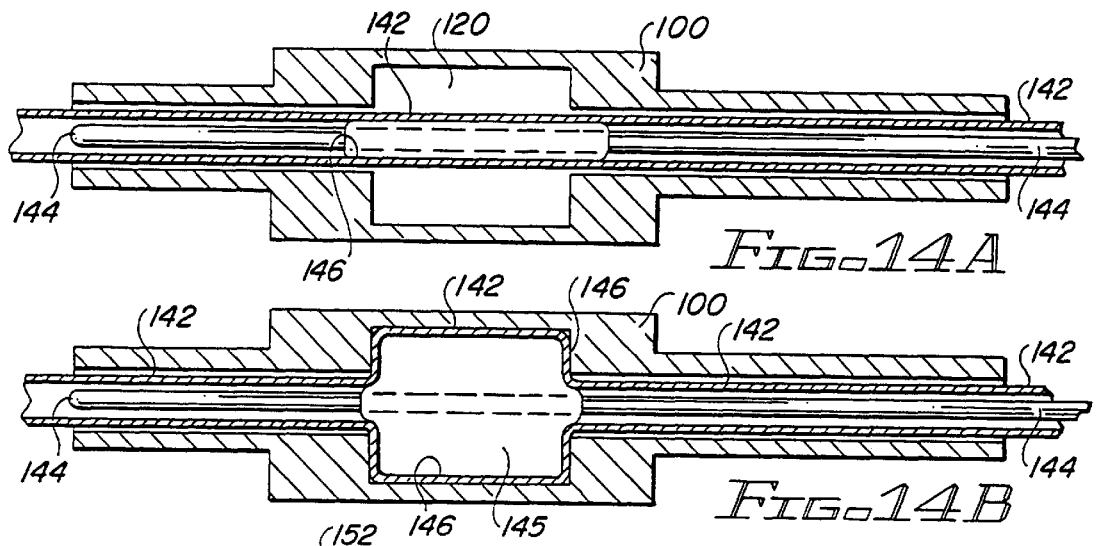
FIG. 14A
FIG. 14B
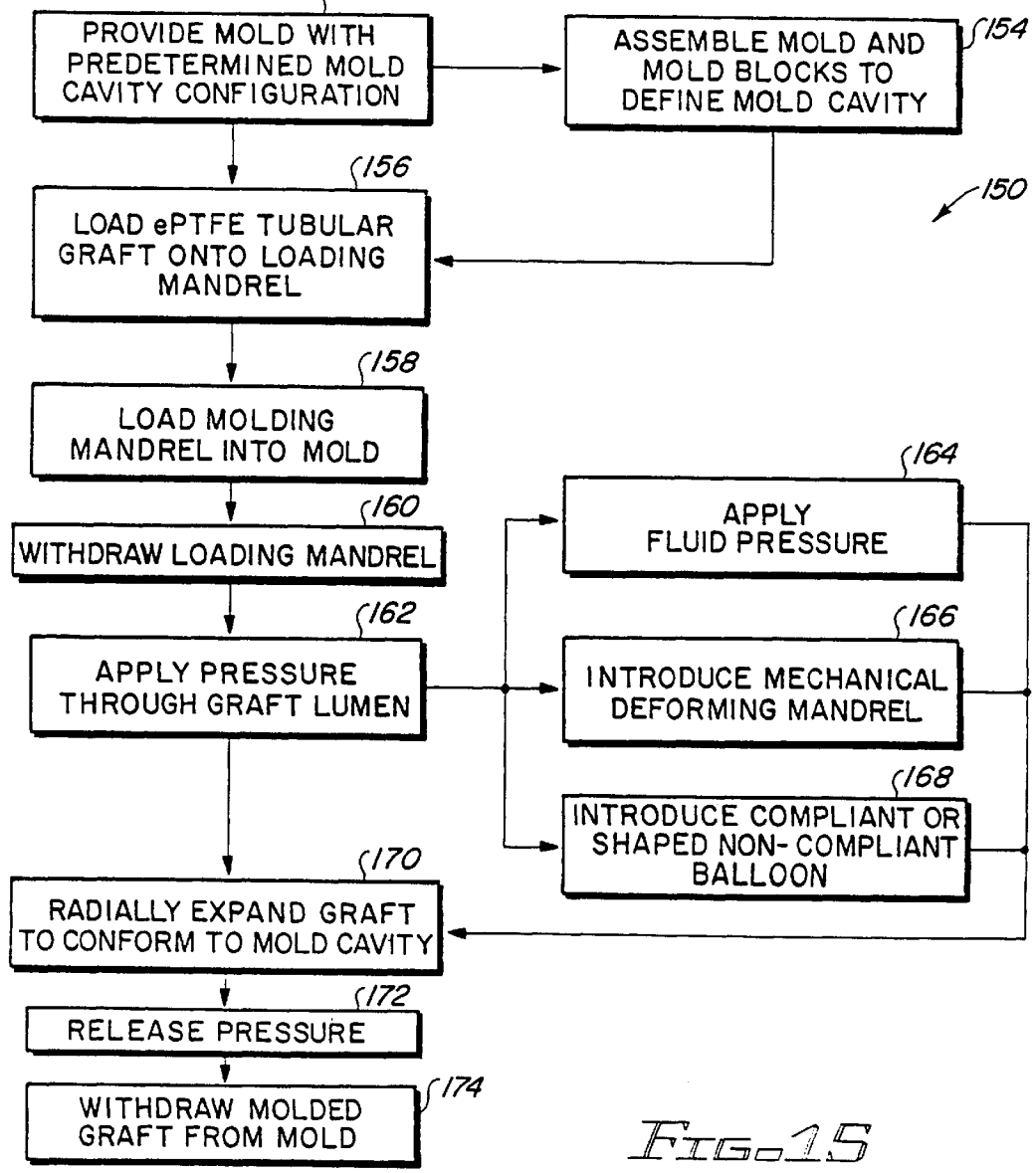
FIG. 15

APPARATUS AND METHOD FOR MAKING FLANGED GRAFT FOR END-TO-SIDE ANASTOMOSIS

CROSS-REFERENCE TO RELATED APPLICATIONS

This application is related to a PCT International Application PCT/US96/02714, which was concurrently filed with the United States Patent and Trademark Office acting as the International Receiving Office under the Patent Cooperation Treaty, entitled "Flanged Graft for End-to-Side Anastomosis," now U.S. Ser. No. 09/125,907. U.S. Ser. No. 09/125,907 is commonly assigned to IMPRA, Inc., the Applicant hereof who hereby expressly incorporates U.S. Ser. No. 09/125,907 by reference thereto as further denoted herein.

BACKGROUND OF THE INVENTION

1. Field of the Invention

The present invention relates generally to vascular grafts, and more particularly to a method and apparatus for forming the flanged polytetrafluoroethylene (PTFE) cuffed section from a tubular PTFE graft to form a flanged vascular graft for end-to-side anastomosis useful for purposes of bypassing an occluded or diseased section of a blood vessel or as an access graft for hemodialysis. The PTFE graft has an integral terminal PTFE flanged cuff section which permits an end-to-side anastomosis with a blood vessel in which the terminal PTFE flanged cuff section is sutured to the blood vessel and provides a PTFE-tissue interface between the graft and the blood vessel. The flanged PTFE graft is the subject of U.S. Ser. No. 09/125,907, which is hereby expressly incorporated by reference as being illustrative of types of flanged grafts useful for distal bypass or hemodialysis access grafts which may be made using the apparatus and method of the present invention.

2. Description of the Prior Art

The uses of cuff grafts for bypassing peripheral vascular occlusive conditions, particularly femoro-crural patch prostheses, or for hemodialysis access grafts are well known in the art. To date, however, either autologous grafts or synthetic grafts with a terminal cuff fashioned from venous tissue at the anastomotic site have been used. Examples of conventional cuffed grafts are the Miller collar described in J. H. Miller, *The Use of the Vein Cuff and PTFE*, in VASCULAR SURGICAL TECHNIQUES 2 ed., 276–286 (W. B. Saunders 1989), and the Taylor patch described in Taylor, R. S., et al, Improved technique for polytetrafluoroethylene bypass grafting: long-term results using anastomotic vein patches, *Br. J. Surg.*, 79:348–354 (1992). Both the Miller graft and the Taylor graft are cuff grafts and each employs a PTFE graft with an autologous venous cuff at the anastomotic site. The Miller collar and the Taylor patch each use venous tissue at the anastomotic site to avoid a compliance mismatch at the PTFE-tissue interface.

The flanged PTFE graft in U.S. Ser. No. 09/125,907, hereby incorporated by reference, offers a new type of anastomosis for femoro-crural bypass or access grafting in which the graft is fabricated in a flared, double-bulb configuration. The inventive graft configuration offers an optimal geometry for the anastomosis as a function of hemodynamic properties. By optimizing blood flow from the bypass prosthesis to the artery, formation of intimal hyperplasia may be reduced with a concomitant increase in graft patency and decreased morbidity.

The apparatus of the present invention consists of an annular mold having a radially extending annular slot, forming an expansion port. The flanged cuff graft is made by first forming an unsintered tubular PTFE vascular graft by extruding a PTFE lubricant mixture into a billet to form a tubular extrudate, placing the extrudate in the annular mold, and forming an annular cuff by either: 1) application of a negative pressure to the expansion port, or 2) application of positive pressure, as by a highly compliant angioplasty balloon, through the tubular extrudate lumen, to radially displace a section of the tubular extrudate, thereby forming a cuffed graft.

Various different approaches have been taken to fabricate branched grafts. As early as 1938, U.S. Pat. No. 2,127,903 to Bowen disclosed a bioabsorbable surgically implantable graft made of animal tissue and a binder formed by wrapping strips of the treated animal tissue about a structural form. U.S. Pat. No. 4,909,979, issued Mar. 20, 1990 to Possis, discloses a method of shaping a human umbilical cord for use as a vascular graft. The method employs a mandrel to support and shape the umbilical cord during forming and curing of the cord. The forming and curing process provides a cord with a blood flow restrictor section. PTFE coatings are provided on the mandrel to facilitate mounting the umbilical cord onto the mandrel. A shaping section of the mandrel is provided with a plurality of vacuum openings in the mandrel. The umbilical cord is treated with ethanol and a vacuum applied until the cord is dehydrated. The cord is then exposed to a curative and fixative solution and a vacuum applied until the umbilical cord is cured substantially airtight and circumferentially compressed and compacted around the mandrel forming section.

U.S. Pat. No. 4,354,495, issued Oct.19, 1982 to Bodicky, discloses a method of connecting a PTFE tube to a hub made of a moldable plastic, e.g., polyurethane, acrylics, polyethylene, polycarbonates, etc. The method involves selectively heating a portion of the PTFE tube to form a bulge or protrusion, then inserting the bulge into a mold and molding the moldable plastic hub about the bulge in the mold. U.S. Pat. No. 4,957,508, issued Sep.18, 1990 to Kaneko et al., discloses an elastomeric medical tube having proximal and distal ends, outwardly flared. The outward flare of the ends is achieved by forming the inner and outer surfaces of the tube to exhibit inverse elastomeric properties, i.e., the inner surface exhibits a dilating force, while the outer surface exhibits a shrinking force. The tube is made of high molecular weight polymers, particularly, polyvinyl halide, polystyrene, polyolefin series polymers, polyester series condensates, cellulose series high polymers, polyurethane series high polymers, polysulfone series resins, polyamides, etc. along with copolymers or mixtures of these.

U.S. Pat. No. 5,387,236 to Noshiki et al., issued Feb. 7, 1995, discloses a vascular prosthesis and method of making a vascular prosthesis by providing a vascular prosthesis substrate made of PTFE or other microporous material, and depositing and capturing within the wall of the prosthesis substrate fragments of biological tissue. The biological tissue fragments may be vascular tissues, connective tissues, fat tissues and muscular tissues and/or vascular endothelial cells, smooth muscle cells and fibroblast cells. The impregnation process is conducted by depositing the cellular material on the inner wall of the graft and applying a pressure differential between the lumenal and ablumenal wall surfaces to drive the tissue fragments into the microporous matrix of the vascular prosthesis. U.S. Pat. No. 4,883,453 to Berry et al., issued Nov. 28, 1989, discloses an aorto-coronary bypass graft and a method of making the graft. The graft consists of a plate portion and at least one tube portion extending from the plate portion. The graft and plate are disclosed as being made of an electrostatically-spun fibrous structure. The graft is adhered to the plate by mounting the graft onto a mandrel, applying adhesive to the surface of the plate surrounding an opening in the plate, and passing the mandrel through an opening in the plate until the graft contacts the adhesive. The adhesive is any suitable adhesive for the materials forming the plate and the graft. According to the preferred embodiment described in this reference, the graft preferably has a tapered wall thickness, such that the graft wall thickness adjacent the plate is greater than that distant the plate.

U.S. Pat. No. 5,110,526 to Hayashi et al., issued May 5, 1992, discloses a process for producing molded PTFE articles. According to this process, unsintered PTFE extrudates are inserted into a sintering mold. The sintering mold has a diameter slightly larger than the outside diameter of the unsintered PTFE extrudate. Clearance between the outside diameter of the unsintered PTFE extrudate and the inside surface of the sintering mold is on the order of 2% of the diameter of the sintering mold. The extrudate is drawn into the sintering mold via a plug, inserted into the terminal lumen of the extrudate and a wire and take-up reel. The PTFE extrudate is cut to match the length of the sintering mold, and the sintering mold is sealed on the cut extrudate end. The assembly is transferred to a sintering oven and sintered. During sintering, the extrudate expands in contact with the sintering mold and conforms to the shape of the sintering mold. After cooling, the sintered extrudate contracts away from the sintering mold and assumes an even shape corresponding to the sintering mold.

U.S. Pat. No. 3,196,194 to Ely, Jr., et al., issued Jul. 20, 1965, discloses an extrusion process for making FEP-fluorocarbon tubing. The extrusion process consists of screw-extruding fluid FEP copolymer through a barrel extruder to form a tubular extrudate, placing the tubular extrudate into a heater, pressurizing the tubular extrudate to radially expand the FEP extrudate, and cooling the expanded extrudate to yield a heat shrinkable tube with memory function to the reduced diameter extrudate.

U.S. Pat. No. 4,503,568 to Madras, issued Mar. 12, 1985, discloses an arterial bypass prosthesis for end-to-side anastomosis and reduction of anastomotic hyperplasia. The arterial bypass prosthesis consists generally of a connector element including a tubular entrance member, a tubular exit member and a heel member. The tubular entrance receives and provides an entrance passage for blood flow. The tubular exit member is coupled to and angularly offset from the tubular entrance and provides a passage for the blood from the entrance member. The heel member extends substantially coaxially from the exit member. The distal end of the heel member is inserted through the open arteriotomy and into the portion of the vessel upstream of the arteriotomy. The heel may be solid or may include a passage continuous with the entrance and exist members. A throat portion is located intermediate the tubular entrance and exit members and a circumferential skirt substantially surrounds the throat portion. The skirt heals into the advential tissue of the blood vessel.

With particular reference to known methods for making PTFE materials, the following are cited as examples of the state and scope of the art. U.S. Pat. No. 4,482,516 to Bowman et al., issued Nov. 13, 1984, discloses a process for producing high strength expanded PTFE products having a coarse microstructure. The resulting PTFE microstructure is then defined by a "coarseness" index which purports to consider node size, i.e., height and width and fibril length.

U.S. Pat. No. 5,376,110 to Tu et al, issued Dec. 27, 1994, discloses a method of making vascular grafts by collagen cross-linking conducted under the influence of alternating pressure across the graft wall. The alternating pressure aids in cross-linking the collagen fibers. U.S. Pat. No. 4,743,480 to Campbell et al., issued May 10, 1988, discloses a method for extruding and expanding tubular PTFE products in which a helical groove is machined into the extrusion barrel and/or the mandrel. Extrusion of a tubular PTFE product results in an extrudate having nodes angularly displaced between about 85–15 degrees from the longitudinal axis of the extrudate.

Finally, U.S. Pat. No. 4,234,535 to Okita, issued Nov. 18, 1980, discloses a process for forming expanded PTFE vascular grafts having fibers of smaller diameter at the inner surface of the tubing and fibers of at least two times diameter at the outer diameter of the tubing. The grafts are produced by a process in which PTFE tubular extrudates are formed, then placed onto drive and take-up capstans. The capstan drive system conveys the extrudate through a heater set at a temperature above 327° C., then into a vacuum case which causes radial expansion of the extrudate at a temperature above 327° C., then, after radial expansion, the vacuum case is cooled, by introduction of cooled air, to a temperature below sintering temperature, thereby fixing the tube at the expanded diameter and in the longitudinal direction by tension from the drive and take-up capstans. This patent also discloses and claims the use of cooling air conveyed through the tube lumen during the radial expansion process. By conveying cooled air through the tube lumen, the temperature at the lumenal surface is maintained below the PTFE sintering temperature. In this manner, differing fibril diameters at the lumenal and ablumenal surfaces are formed.

In current clinical practice, a peripheral anastomosis between a bypass or access prosthesis and a peripheral artery has been performed by either direct anastomosis, interposition of a venous segment at the anastomotic site, anastomosing the prosthesis with a long venous patch sutured into the artery (Linton Patch), enlargement of the prosthesis within the anastomotic region using a venous patch (Taylor Patch) or interposition of a venous cylinder between the prosthesis and the artery (Miller Collar). In femoro-distal grafting, there is growing evidence that compliance mismatch between the graft and the recipient artery and hemodynamic factors are a major cause of thrombosis and the development of subintimal hyperplasia at the anastornotic site.

BRIEF SUMMARY OF THE INVENTION

It is a principal object of the present invention to provide a new graft for access or femoro-distal bypass grafting made of microporous expanded polytetrafluoroethylene (ePTFE).

It is a further object of the present invention to provide an access or femoro-distal bypass graft made of ePTFE having a distal flange suitable for femoro-crural bypass grafting.

It is a further object of the present invention to provide an access or femoro-distal bypass graft made of ePTFE having a distal flange suitable for arterio-venous patch (AVP) grafting.

It is a further object of the present invention to provide an apparatus and method for making a new graft for access or femoro-distal bypass grafting.

It is a still further object of the present invention to provide an apparatus and method for making a new graft for access or femoro-distal bypass grafting utilizing a tubular mold having a circumferential recess extending radially from the central axis of the tubular mold to form a distal flange on a tubular polytetrafluoroethylene graft.

These and other objects, features and advantages of the present invention will be more apparent to those skilled in the art from the following more detailed description of the preferred embodiments of invention taken with reference to the accompanying drawings.

BRIEF DESCRIPTION OF THE DRAWINGS

FIG. 8 is an exploded elevational view of the inventive apparatus for making the inventive graft.

FIG. 9 is a cross-sectional view taken along lines 9—9 of FIG. 8 illustrating a first embodiment of a first mold block for forming the inventive graft.

FIG. 10 is cross-sectional view taken along line 10—10 of FIG. 8 illustrating a second embodiment of a first mold block for forming the inventive graft.

FIG. 11 is a cross-sectional view taken along line 11—11 of FIG. 8 illustrating a mold tube for forming the inventive graft.

FIG. 12 is a cross-sectional view taken along lines 12—12 of FIG. 8 illustrating a second mold block for forming the inventive graft.

FIG. 13 is an elevational view of a second embodiment of the mold for forming the graft in accordance with the present invention.

FIG. 14A is a longitudinal cross-sectional view illustrating the inventive molding apparatus, a tubular graft within the molding apparatus, and a balloon catheter within the tubular graft prior to radial expansion of the tubular graft within the molding apparatus.

FIG. 14B is a longitudinal cross-sectional view of the inventive molding apparatus of FIG. 14A, illustrating the tubular graft after radial expansion within the molding apparatus.

FIG. 15 is a flow diagram illustrating the method for making the inventive femoro-distal bypass graft in accordance with the preferred embodiments of the present invention.

DETAILED DESCRIPTION OF THE INVENTION

Figure 1:
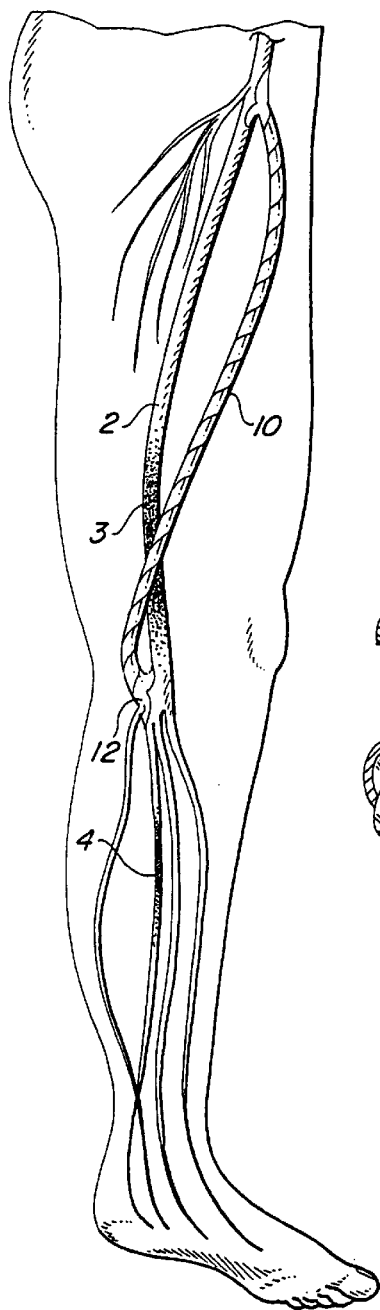
FIG. 1 is a diagrammatic representation of peripheral vasculature in a human leg, illustrating an implanted femoro-crural bypass graft.

FIG. 1 illustrates a sequential femoro-posterior tibial bypass with a PTFE graft to an isolate popliteal segment and a distal graft. The use of a PTFE graft 2 bypassing an occluded section 3 of the femoral artery or an occluded section 4 of the popliteal artery to restore distal circulation is well known. As noted above, various cuff and patch techniques have been devised.

Figure 2:
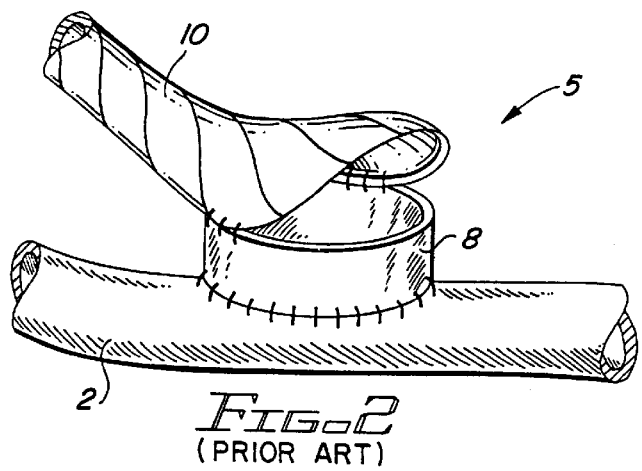
FIG. 2 is a diagrammatic representation a prior art Miller Collar.

FIG. 2 illustrates a Miller collar 5 in which a venous segment 8, typically 3–4 cm of the saphenous vein, is obtained and sutured to an open arteriotomy in the popliteal or tibial arteries to form a cylindrical cuff 8 extending outwardly from the artery 2. The venous segment 8 is fashioned into a collar by opening it longitudinally and anastomosing it to the arteriotomy using a 6/0 or 7/0 prolene suture. The collar is then closed with a 6/0 prolene suture. An ePTFE graft 10 is cut to match the circumference of the collar and then anastomosed to the collar using a continuous 5% prolene suture. The Miller collar 5 is indicated in situations where PTFE is to be anastomosed to tibial arteries, the popliteal artery, or in sequential bypass procedures, e.g., femoro-popliteal-tibial bypass.

Figure 3:
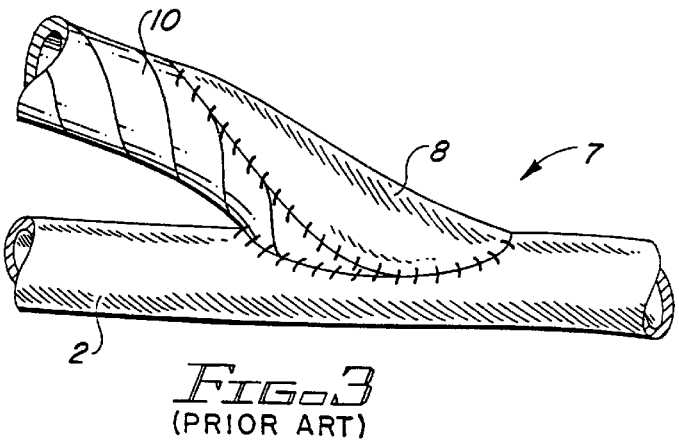
FIG. 3 is a diagrammatic view of a prior art Taylor Patch.

FIG. 3 illustrates a Taylor patch 7. In a Taylor patch 7 procedure, a length of vein 5–6 cm long is harvested, typically from an available segment of saphenous vein. The harvested vein is opened longitudinally and trimmed to form a diamond-shaped vein patch 8. A distal end of an ePTFE graft 10 is trimmed to a U-shaped open end and a V-shaped slot along an upper surface of the ePTFE graft 10. The U-shaped open end of the ePTFE graft forms the ePTFE-arterial suture line, while the V-shaped slot is sutured to the venous patch 8. The vein patch 8 is laid along the V-shaped slot in the ePTFE graft 10 and the open arteriotomy in the correct orientation and sutured to both the ePTFE graft 10 and the arteriotomy. The suture line extends from a heel of the graft to the toe of the graft about the arteriotomy to complete the Taylor patch bypass graft.

Graft patency for standard end-to-side ePTFE graft/arterial anastomoses has been reported between 21 and 60% for one year patency and between 14 and 38% for three year patency. One year patency using the Miller collar has been reported at 47% for ePTFE crural grafts, with three year patency being 52%. One year patency using the Taylor patch has been reported at 86%, with three year patency being reported at 61%. Chester, J. F., et al, "Interposition vein patches for vascular reconstruction," *Hospital Update*, Feb. 1993. Direct PTFE to artery anastomosis has been criticized because of mechanical distortion of the artery by the relatively rigid PTFE and formation of intimal hyperplasia between the PTFE and the recipient artery. These two factors have been implicated in the high occlusion rates and low graft patency characteristic of direct PTFE to artery anastomoses. C. W. Jamison, et al, VASCULAR SURGERY, 330–340 (5th ed. 1994).

Figure 4B:
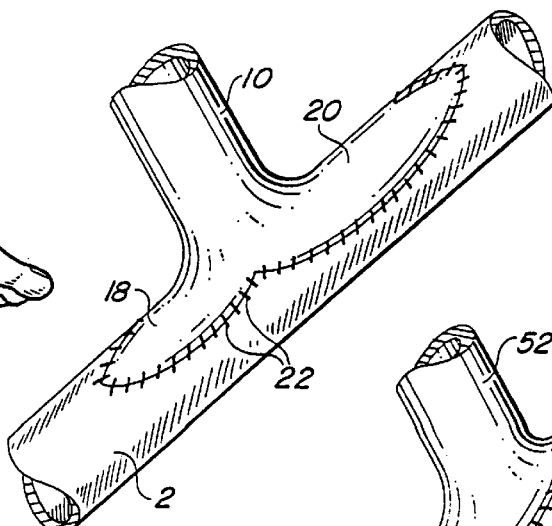
FIG. 4B is a perspective view of the inventive graft for hemodialysis access or femoro-crural bypass anastomosed to a section of the peripheral vasculature.
Figure 4B:
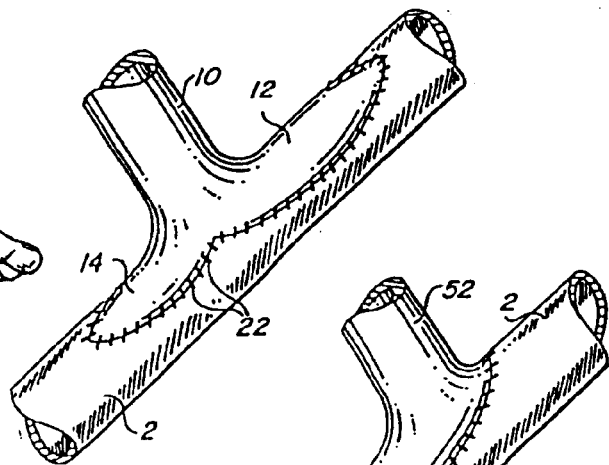
Figure 4A:
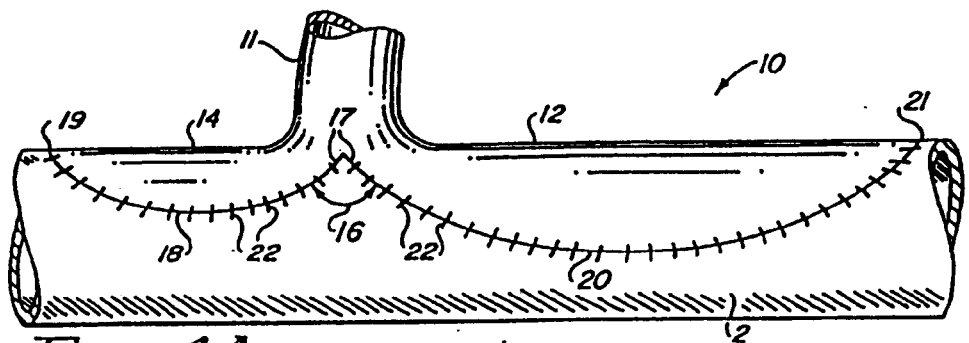
FIG. 4A is a diagrammatic representation of the inventive graft for hemodialysis access or femoro-crural bypass anastomosed to a peripheral artery.

The preferred embodiments of the flanged graft are illustrated in FIGS. 4A–6B. As illustrated in FIG. 4A, a first embodiment of the flanged graft 10 is a bifurcated double bulb configuration in which an ePTFE tubular graft 11 has a distal bifurcation, forming flanges 12 and 14. In a distal end-to-side anastomosis the distal end of the graft 11 is anastomosed to an open arteriotomy formed in the wall of a receiving artery 2. The bifurcated flanges 12 and 14 project in opposing directions substantially perpendicular to the central longitudinal axis of the graft 11 to facilitate the anastomosis, increase compliance matching between the ePTFE graft 11 and the receiving artery 2, and to optimize hemodynamic flow from the graft 11 into the receiving artery 2. When the graft 11 is positioned in an end-to-side relationship with the receiving artery 2, each of the bifurcated flanges 12 and 14 lie substantially parallel to the longitudinal axis of the receiving artery 2 and extend in the proximal and distal directions relative to the receiving artery 2. The bifurcated flanges 12 and 14 preferably have an elongated bulbous configuration which permits the bifurcated flanges 12 and 14 to be circumferentially positioned substantially co-incident with the curvature of the receiving artery 2 and subtending the open arteriotomy (not shown). Bifurcated flanges 12 and 14 are each preferably formed to have a substantially elliptical shape with outer arcuate peripheral edges 20 and 18 terminating in toe portions 21 and 19 respectively. A heel region 17 is immediately contiguous with the tubular graft 11 and each of the arcuate peripheral edges 20 and 18 of bifurcated flanges 12 and 14. The juncture between the peripheral edge 20 of flange 12 and the peripheral edge 18 of flange 14 at the heel region 17 form a crotch angle 16. Crotch angle 16 is preferably between 45 and 180° to maximize the strength of the graft at heel region 17.

The bifurcated flanges 12 and 14 may be symmetrical or asymmetrical relative to one another. The selection of symmetrical or asymmetrical bifurcated flanges 12 and 14 is preferably determined by the vascular surgeon based upon the identity of the receiving artery 2, the position of the arteriotomy on the receiving artery 2 and the lumenal diameter of the graft 11. The graft 11 is preferably anastomosed to the receiving artery 2 using continuous sutures 22 to join the arteriotomy to the peripheral edges 20 and 18 of the bifurcated flanges 12 and 14, the heel region 17 and the crotch angle 16. FIG. 4B depicts a perspective view of the first embodiment of the graft 10 anastomosed to a receiving artery 2.

Figure 5:
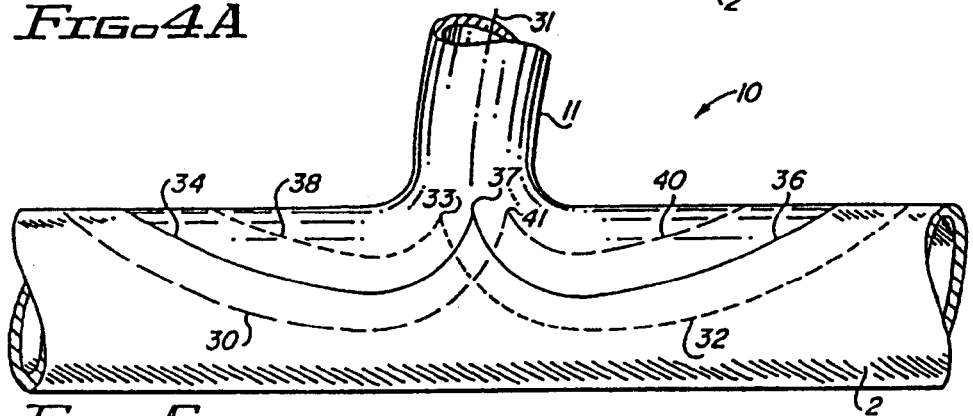
FIG. 5 is a diagrammatic representation of alternative configurations of the inventive graft for hemodialysis access or femoro-crural bypass anastomosed to a peripheral artery.

FIG. 5 illustrates various sizes and symmetries of the bifurcated flanges at the distal end of a tubular ePTFE graft 11 anastomosed to a receiving artery 2. A first graft has asymmetrical bifurcated flanges 30, 40 in which flange 30 has a greater surface area than flange 40, with flange 30 extending laterally from and circumferentially about the graft 11 a greater extent than flange 40. The crotch angle 41 of the first graft is offset toward the shorter flange 40 relative to the median line 31 of the graft 11. The configuration of the first graft having flanges 30, 40 is well suited to end-to-side anastomoses where the angular orientation between the graft 11 and the receiving artery 2 is oblique on the side of the shorter flange 40 and obtuse on the side of the longer flange 30.

A second graft has substantially symmetrical bifurcated flanges 34, 36, with the crotch angle 37 being substantially co-incident with the median line 31 of the graft 11. Both of flanges 34 and 36 extend substantially identical lengths laterally and in opposite directions relative to the graft 11 and the arcuate peripheral edges of the flanges 34, 36 extend circumferentially about the receiving artery 2 to a substantially equivalent extent. The second graft with symmetrical bifurcated flanges 34, 36 is particularly useful where the angular orientation of the end-to-side anastomosis between the graft 11 and the receiving artery 2 is substantially perpendicular.

The third graft, denoted by asymmetrical bifurcated flanges 38, 32, is substantially a mirror image of the first graft, denoted by asymmetrical bifurcated flanges 30, 40. In this third graft, the flange 32 projects laterally from and extends circumferentially about the graft 11 a greater extent than flange 38. The crotch angle 33 of the third graft is offset toward the shorter flange 38 relative to the median line 31 of the graft 11. The configuration of the third graft, having flanges 38, 32 is well suited to end-to-side anastomoses where the angular orientation between the graft 11 and the receiving artery 2 is acute on the side of the shorter flange 38 and obtuse on the side of the longer flange 32.

In each of the three preferred embodiments of the bifurcated flange graft 10, the bifurcated flanges are preferably made of ePTFE and formed as a continuous, integral, monolithic section of the ePTEE tubular graft 11, without intervening seams or overlap regions.

From the foregoing, those skilled in the art will understand that the use of asymmetrical bifurcated flanges on the flanged graft 10 is particularly well suited to end-to-side anastomoses where the longitudinal axis of the inflow graft is positioned at an acute angle relative to the receiving artery 2, with the longer flange being distally-oriented and the shorter flange being proximally oriented relative to the direction of blood flow.

Dimensionally, it is preferable to fabricate each bifurcated flange to a length which is between 1 to 5 times the lumenal diameter of the graft. Thus, for a 5 mm graft, the shorter flange should be no less than 5 mm in length measured from the outer surface of the graft to the furthest point on the toe region of the flange, and the longer flange should be no greater than 25 mm, measured from the outer surface of the graft to the furthest point on the toe region of the flange. Circumferentially, each bifurcated flange should extend no greater than 1 times the lumen diameter of the graft about the receiving artery. Thus, where a graft has a lumenal diameter of 5 mm, the bifurcated flange should extend no further than 5 mm measured from the median line of the graft to a point on the arcuate peripheral edge of the flange which is circumferentially furthest from the median line of the graft. These dimensional constraints have been found to represent optimal parameters for an ePTFE femoro-infragenicular bypass graft which does not use a venous patch or collar at the ePTFE-arterial junction. The configuration of bifurcated flanged graft 10 has been found to have an optimal geometry and a reduced probability of developing subintimal hyperplasia as a cause of graft failure. The inventive bifurcated flanged graft 10 has shown minimal presence of zones of low flow velocity or vortex formation at the anastomotic site and exhibits an optimal hemodynamic flow pattern for an end-to-side anastomosis.

Conventional end-to-side anastomoses exhibit complex hemodynamic flow patterns at the anastomotic junction. Zones of low flow velocity, reversed flow velocity and vortex formation are found in virtually all types of known end-to-side anastomoses. Clearly, detailed hemodynamic measurements are difficult to obtain in vivo. A pulsatile flow model was developed to simulate hemodynamic conditions within the distal end-to-side anastomosis of the inventive femoro-infragenicular bypass graft 10. A closed flow loop system was made by connecting two reservoirs maintained at systolic and diastolic pressure. A magnetic valve was used to generate a pulsatile flow representative of that in the femoral arteries. A blood-analog fluid (7.5% Dextran by weight in distilled water) was used. To enhance sonographic visualization, the blood-analog fluid was seeded (1 g/L) with 40–120 m SEPHADEX particles (Pharmacia, Uppsala, Sweden). Flow visualization and velocity field measurements were accomplished by direct dye injection and Doppler color flowometry using real-time ultrasonography (Acuson 128 XP/10) with a 5 MHZ linear array transducer having a Doppler frequency of 3.5 MHZ and an aperture size of 3.8 cm. Doppler color flowometry images were continuously recorded using an S-VHS video camera and an S-VHS high resolution video cassette recorder. Images were obtained at specific intervals within the pulsatile cycle using a peak capture techniques which map peak velocities at each pixel in the frame during successive one second intervals. Flow velocity measurements were detected using ultrasound beams transmitted at an angle of 70° to the face of the transducer in an upstream or downstream direction.

Figure 7:
FIG. 7 is a diagrammatic representation of the hemodynamic flow profile through the inventive graft.

The bifurcated flanged graft 10 was tested against the Linton patch and the Taylor patch using the dye injection and Doppler color flowometry flow visualization techniques under both low and high pulsatile flow rates. In both the Linton patch and the Taylor patch, the velocity profile was skewed toward the outer wall of each graft, independent of flow rates. An impingement of the flow stream on the outer wall produced circumferential flow motions in the high flow situation, while under low flow conditions, a region of flow stagnation was identified at the host vessel outer wall and in line with the inner wall of the graft. This point marked a flow split zone where one flow stream moved in the distal branch and one flow stream moved in the proximal branch of the recipient artery. In the inventive bifurcated flanged graft 10, the area of flow splitting was virtually eliminated. Flow vortexing was observed in the toe and heel regions of the Taylor patch and Linton patch was observed. Minimal vortex formation was observed at the anastomotic site of the inventive bifurcated flanged graft 10. The flow profile through the inventive bifurcated flanged graft 10 is depicted in FIG. 7.

Under Doppler color flowometry, both the Linton patch and the Taylor patch produced the following hemodynamic profiles: 1) flow splitting into reversed vortex flow in the upstream and forward flow in the downstream direction, 2) flow jetting and a non-homogeneous flow pattern downstream of the anastomotic site, and 3) low flow regions with zero flow or reverse flow. The primary location for each of these hemodynamic phenomenon were opposite to the graft inlet and along the inner wall of the artery from the toe of the anastomosis to downstream. Variation of flow patterns with deceleration of flow waveform from systole to diastole resulted in and increase of low flow regions in both the Linton patch and the Taylor patch. None of these hemodynamic phenomena were observed with any degree of statistical significance with the inventive bifurcated flanged graft 10, which exhibited a substantially laminar flow pattern illustrated in FIG. 7.

In a clinical study, 65 infragenicular bypass grafts using the inventive bifurcated flanged graft 10 were performed on 62 patients. In 18 of the patients, a temporary extracorporeal bypass was inserted between the proximal and distal anastomotic sites for measurement of blood flow and pressure to calculate the peripheral arterial resistance in each of the upstream and downstream directions. Patency of the inventive grafts was tracked. Prior to the bypass operation, all patients underwent Doppler ultrasonographic ankle artery pressure measurements and arteriography. Graft patency was tracked by clinical examination and Doppler ultrasonographic arterial pressure studies on all patients at three month intervals. The morphology of the anastomosis was examined postoperatively by angiography and at each three month interval with Doppler color flowometry. The one year primary patency rate was 60% which remained constant over the second year of follow up. The one year secondary patency rate was 68% while the second year patency rate fell only to 60%.

Figure 6B:
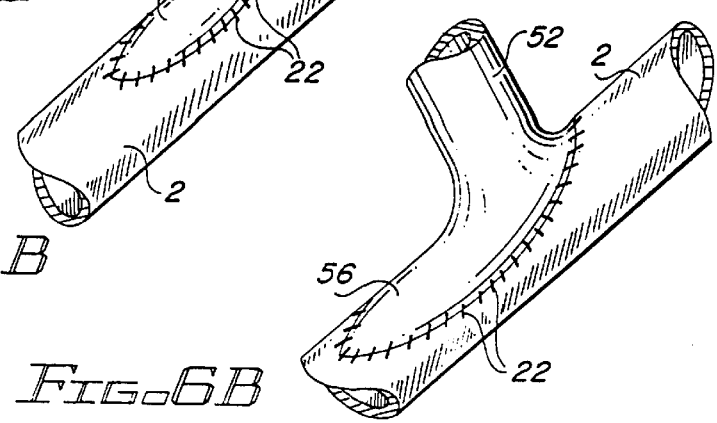
FIG. 6B is a perspective view of the inventive graft for hemodialysis access or AVP bypass.
Figure 1:
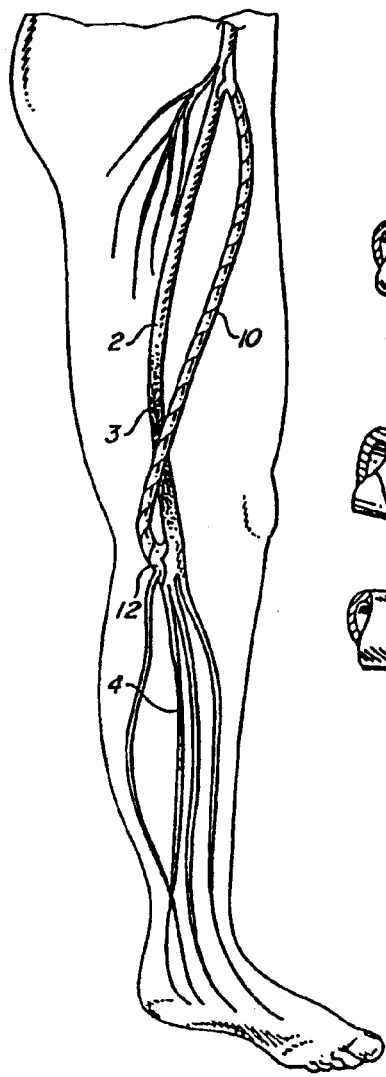
Figure 2:
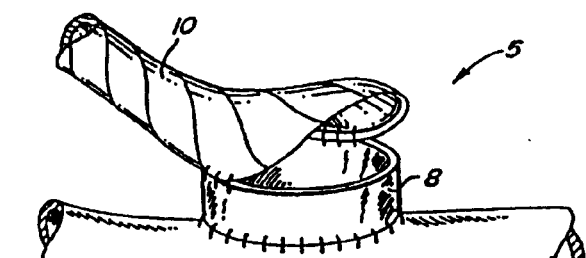
Figure 3:
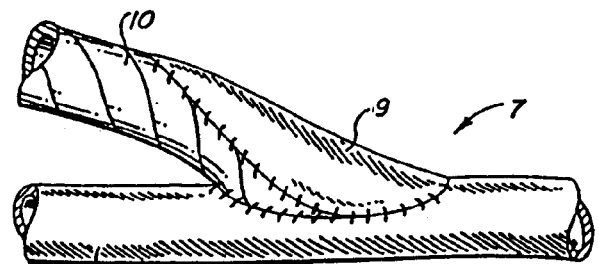
Figure 6B:
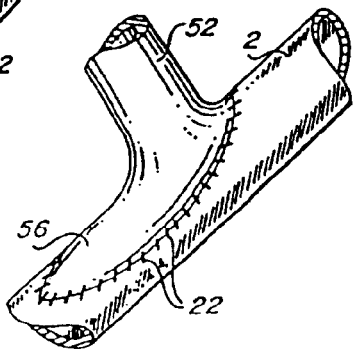
Figure 6A:
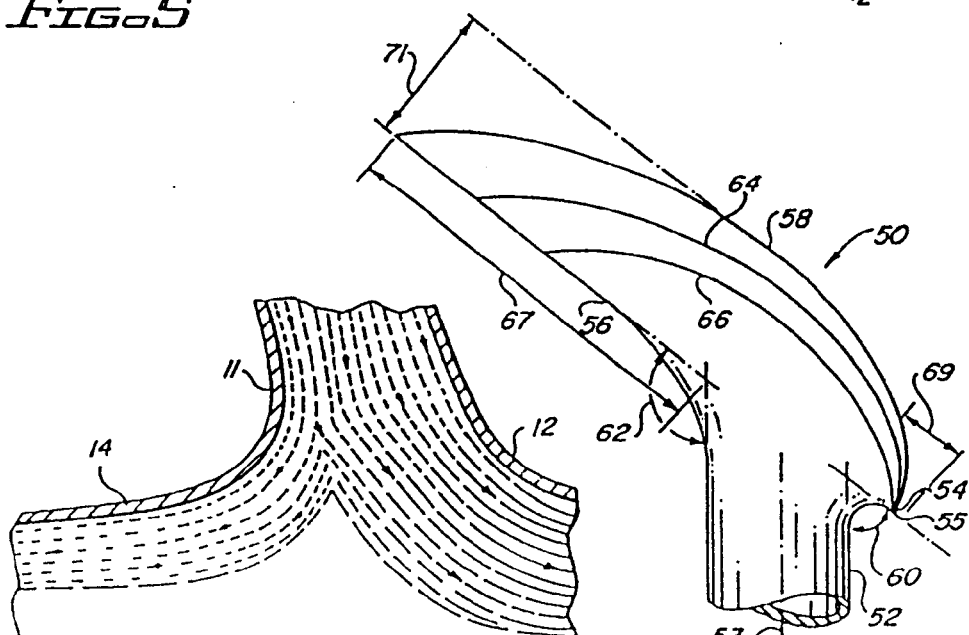
FIG. 6A is a diagrammatic representation of the inventive graft for hemodialysis access or AVP bypass.

Turning now to FIGS. 6A and 6B, there is shown a second preferred embodiment of the bypass graft, referred to for purposes of identification as the arterio-venous patch (AVP) prosthesis 50. The AVP prosthesis 50 consists generally of a tubular ePTFE graft member 52 which has an outwardly flared skirt 56 which extends circumferentially about the tubular ePTFE graft member 52. The flared skirt 56 preferably has a generally elliptical shape and is offset from a central longitudinal axis 53 of the tubular ePTFE graft member 52, such that one focal point of the elliptically shape flared skirt 56 is positioned a greater distance from the central longitudinal axis 53 of the tubular ePTFE graft member 52 than another focal point of the elliptically shaped flared skirt 56. Additionally, the flared skirt 56 resides in a plane 55 which is distally and angularly offset relative to the central longitudinal axis 53 of the tubular ePTFE graft member 52. By being distally and angularly offset relative to the central longitudinal axis 53 of the tubular ePTFE graft member 52, the flared skirt 56 forms a toe angle 62 and a heel angle 60 with the tubular ePTFE graft member 52. In accordance with the preferred embodiments of the AVP prosthesis 50, the toe angle 62 is greater than 90° relative to the central longitudinal axis 53 of the tubular graft member 52, while the heel angle 60 is less than 90° relative to the central longitudinal axis 53 of the tubular graft member 52. In accordance with the preferred embodiments of the present invention, it is preferable that the toe angle 62 be within the range of 95° to 160° relative to the central longitudinal axis 53 of the ePTFE tubular graft member 52, while the heel angle 60 be within the range of 20° to 85° relative to the central longitudinal axis 53 of the ePTFE tubular graft member 52.

Flared skirt 56 has a toe section 67 which projects outwardly from the ePTFE tubular member 52 at toe angle 62. The length of toe section 67 may be predetermined during manufacture, or may be trimmed by a vascular surgeon during the implant procedure to accommodate the open arteriotomy at the anastomotic site. A heel section 69 projects outwardly from the ePTFE tubular member 52 at heel angle 60, and in an opposing direction from the toe section 67. A curved outer peripheral edge 58 of the flared skirt 56 subtends a 180° arc and forms a continuous surface interconnecting toe section 67 and heel section 69. Depending upon the desired length of toe section 67, the length of curved outer peripheral edge 58 and the extension distance 71 which the flared skirt 56 projects in the distal direction relative to the ePTFE tubular member 52 will vary. Phantom lines 64 and 66 depict alternative curved outer peripheral edges 64 and 66 of the flared skirt 56.

The flared skirt 56 is preferably made of ePTFE and is formed as a continuous, integral, monolithic part of the ePTFE tubular graft member 52, without any intervening seam or overlap. As illustrated in FIG. 6B, the flared skirt 56 assumes a curved configuration in its z-axis to enable a suture anastomosis between the outer peripheral edge 58 and about a circumferential aspect of an artery. The flared skirt 56 should, preferably, extend a distance no greater than the lumenal diameter of the ePTFE tubular graft member 52, measured from an upper surface of the toe region 67 to a point along the outer peripheral edge 58 of the flared skirt 56 which is furthest from the upper surface of the toe region 67.

In accordance with the preferred embodiments of the AVP prosthesis 50, the toe region 67 will have a length greater than that of the heel region 69, with the toe region 67 projecting outwardly from the central longitudinal axis 53 of the tubular ePTFE graft member 52 in the direction of the blood flow. As noted above, the length of toe region 67 is variable, preferably within the range of 5 to 25 mm measured from an outer wall surface of the ePTFE tubular graft member 52 adjacent the toe region 67, to a furthest point on the outer peripheral edge 58 of the toe region 67. It has been found preferable, however, to maintain the length of heel region 69 to a fixed length of approximately 3 mm, measured from the outer wall surface of the ePTFE tubular graft member 52 adjacent the heel region 69, for femoro-distal bypass anastomoses.

The foregoing preferred embodiments of the flanged bypass grafts 10 and 50 may be made by the following described inventive method using the following described inventive apparatus for making the flanged bypass grafts 10 and 50. FIGS. 8–13 depict alternative embodiments of molding apparatus 100 and 130 which are preferably used in accordance with the method depicted in the flow diagram at FIG. 15.

With particular reference to FIGS. 8–12, there is depicted a molding apparatus 100 for making the flanged bypass grafts 10 and 50. Molding apparatus 100 consists generally of molding tube 102 having a lumenal cavity 101 which extends through an entire longitudinal length of the molding tube 102 and opens to each of two opposing ends of the molding tube 102. Molding tube 102 further includes a plurality of apertures 112 passing through a portion of a hemispherical cross-section of the molding tube 102. The plurality of apertures 112 are positioned in a linear array extending along a longitudinal axis of the molding tube 102 and positioned at each opposing end of the molding tube 102.

A first block member 104 and a second block member 106, each having a tubular shape and an outer diameter configured to be reciprocally engageable within the lumenal cavity 101 of molding tube 102, are provided. First block member 104 has a longitudinally oriented lumen 105 which extends through an entire longitudinal length of first block member 104 and is open at each of two ends of the first block member 104. First block member 104 has a planar face 108 which is oriented non-perpendicular relative to the longitudinal axis of the first block member 104. A plurality of apertures 112 extend through the first block member 104 and are positioned as a longitudinal array with each aperture 112 positioned to positionally correspond to the apertures 112 in the molding tube 102. The plurality of apertures 112 in the first block member pass laterally through the first block member 104 intermediate between the longitudinally oriented lumen 105 and an outer diameter of the first block member 104.

Like first block member 104, second block member 106 has a longitudinally oriented lumen 107, which extends through an entire longitudinal length of the second block member 106, is open at each of two ends of the second block member 106 and is co-axial with the lumen 105 of the first block member 104. Second block member 106 has a planar face 110 which is oriented non-perpendicular relative to the longitudinal axis of the second block member 106 and is substantially parallel to planar face 108 of the first block member 104. A plurality of apertures 112 extend through the second block member 106 and are positioned as a longitudinal array with each aperture 112 situated to positionally correspond to at least some of the apertures 112 in the molding tube 102. The plurality of apertures 112 in the second block member 106 pass laterally through the second block member 106 intermediate between the longitudinally oriented lumen 107 and an outer diameter of the second block member 106.

The molding apparatus 100 is assembled by engaging the first block member 104 within the lumen 101 of the molding tube 102 by inserting the first block member into a first open end of the molding tube 102, aligning at least one of the plurality of apertures 112 in the first block member 104, with at least one of the plurality of apertures 112 in the molding tube 102 and inserting a lock pin 113 into the aligned at least one of a plurality of apertures 112 such that it engages both the molding tube 102 and the first block member 104 in a fixed position relative to one another. The second block member 106 is then engaged within the lumen 101 of the molding tube 102 by inserting the second block member into a second open end of the molding tube 102, aligning at least one of the plurality of apertures 112 in the second block member 106, with at least one of the plurality of apertures 112 in the molding tube 102 and inserting a lock pin 113 into the aligned at least one of a plurality of apertures 112 such that it engages both the molding tube 102 and the second block member 106 in a fixed position relative to one another, and the planar faces 108 and 110 of the first block member 104 and the second block member 106 are substantially parallel to one another and in a spaced apart relationship relative to one another defining a molding space 120 therebetween. By providing planar faces 108 and 110 oriented at a desired angle relative to the longitudinal axis of the first 104 and second 106 block members, and parallel to one another, the molding space 120 defined therebetween is bounded by the parallel, angularly displaced faces 108 and 110 and sections of the lumenal wall of the molding cavity 101 and has a generally trapezoidal cross-sectional shape. The depiction of molding tube 102 in FIG. 8 illustrates one embodiment of the molding apparatus 100 in its assembled state by phantom lines.

Also shown in FIG. 8 are alternative embodiments 104' and 106' of the first block member 104 and the second block member 106, respectively. The first alternative embodiment of the second block member 106' is a stepped-diameter lumen first block member 114 in which the longitudinally oriented lumen has a first diameter 116 and a second diameter 117 at different positions along the lumen. By providing a stepped-diameter lumen 115, it is possible to create a taper in the resulting graft proximal to the flange or skirt which is formed within the molding space 120, as will be described in greater detail hereinafter. The second alternative embodiment of the first block member 104' and second block member 106' is virtually identical to the first block member 104 and second block member 106, except that planar faces 124 and 128 are oriented substantially perpendicular to the longitudinal axis of the first block member 104' and the second block member 106'. By providing planar faces 124, 128 oriented substantially perpendicular to the longitudinal axis of each of the first 104' and second 106' block members, the molding space 120 formed therebetween is bound by the perpendicular planar faces 124, 128, and the lumenal diameter of the molding cavity 101 and has a generally rectangular or quadrilinear cross-sectional shape. Any of the first 104 or the second 106 block members, or their alternative embodiments 104' or 106', may include a stepped lumen 105, 107 respectively, as illustrated in connection with the foregoing description of the first alternate embodiment 114 of the second block member. Further, the angular orientation of the face 110 or 124 may be selected as desired depending upon the resulting angular displacement desired for the flange or cuff on the flanged graft made by the inventive apparatus.

FIGS. 9–12 are cross-sectional views of sections of the apparatus for making the inventive flanged bypass graft. FIG. 9 is a cross-sectional view taken through the second block member 106, illustrating the body of the second block member 106, the longitudinally oriented lumen 107 and one of the plurality of apertures 112 passing laterally through the second block member 106. FIG. 10 is a cross-sectional view of the stepped-diameter lumen second block member 114 taken along line 10—10 of FIG. 8. The body of the first block member 114 shown with the central longitudinal lumen 115 passing therethrough, and showing the first lumenal diameter 116, the second lumenal diameter 117 and one of the plurality of apertures 112 passing laterally through the stepped-diameter lumen second block member 114. FIG. 11 is a cross-sectional view of the molding tube 102, taken along line 11—11 of FIG. 8. In FIG. 11, it is seen that aperture 112 passes laterally through the molding tube 102 and opens into the lumen 101 of the molding tube 102 to facilitate alignment with the apertures 112 in the first block member 104, the second block member 106 or the stepped-diameter second block member 114, upon engagement with the molding tube 102, to receive lock pin 113 therethrough. Finally, FIG. 12 is a cross-sectional view taken along lines 12—12 in FIG. 8 and illustrate the body of the first block member 104, the central longitudinal lumen 105 and one of the apertures 112 passing laterally through the body of the first block member 104 without impinging into lumen 105.

It will be understood, by those skilled in the art, that when the molding tube 102, the first block member 104 and the second block member 106 are assembled and secured with a plurality of lock pins 113 inserted into apertures 112, lumen 105 of the first block member 104, and co-axial lumen 107 of the second block member 106, form a common longitudinal lumen 122 which passes through the entire longitudinal axis of the molding apparatus 100 and is open to the two opposing ends of molding tube 102 and to the molding cavity 120. Common longitudinal lumen 122, therefore, affords bilateral access to the molding cavity 120. As will be described in greater detail hereinafter, an expanded polytetrafluoroethylene tubular graft is axially passed into the common longitudinal lumen 122, past the molding cavity 120 so that a longitudinal portion of the ePTFE tubular graft resides in the molding cavity 120. A radially expansive force is then applied to the longitudinal portion of the ePTFE tubular graft resident within the molding cavity 120 which radially expands the longitudinal portion of the ePTFE tubular graft material resident within the molding cavity 120, thereby forming the flange or skirt section of the inventive distal bypass graft. The radially expansive force may be applied either through the graft lumen or external to an outer wall surface section of the longitudinal portion of the ePTFE tubular graft or created by a pressure differential applied across the longitudinal portion of the ePTFE tubular graft within the molding cavity 120.

FIG. 13 depicts a second preferred embodiment of a molding apparatus 130 in accordance with the present invention. As distinguished from the molding apparatus 100 depicted in FIGS. 8–12, the molding apparatus 130 is assembled as a unitary non-adjustable apparatus. Molding apparatus 130 consists of a molding tube 132 having a molding cavity 134, which may be configured in any manner desired to produce a skirt of a flange. The molding cavity 134 may be oriented at a non-perpendicular angle relative to the longitudinal axis of the molding apparatus 130, assuming a trapezoidal longitudinal cross-sectional profile, as depicted in FIG. 13 or perpendicular relative to the longitudinal axis of the molding apparatus 130, assuming a generally rectangular longitudinal cross-sectional profile (not shown). The molding cavity 134 may further be dimensioned such that the volume of mold cavity 134 is selected based upon the size and shape of skirt or flange desired in the resulting flanged distal bypass graft produced in molding apparatus 130. Molding tube 132 further includes opposing laterally projecting port members 133, 135, each having a lumen 138, 137, respectively, which are co-axial relative to one another. Optionally, lumen 138 of port member 133 may have a tapered section 140 which transitions between a diametrically larger or smaller lumen 138. Tapered section 140 of lumen 138 permits a corresponding tapered region to be formed either proximal or distal to the flange or skirt in the inventive flanged distal bypass graft.

Both molding apparatus 100 and 130 are preferably made of either a polymer plastic or metal capable of withstanding pressures up to 100 psi without substantial dimensional distortion. It is further preferable, though not required by the present invention, that both the molding apparatus 100 and 130 also be made of a high temperature material capable of being exposed to temperatures in excess of at least the crystalline melt point temperature of polytetrafluoroethylene, i.e., 327° C., and preferably up to and including 450° C., without substantial dimensional distortion.

A wide variety of methods may be used to apply a radially expansive force to the longitudinal section of ePTFE resident within the molding apparatus 100 and 130, particularly the longitudinal section of ePTFE resident within the molding cavities 120 and 134. In accordance with the best mode contemplated for the invention, a compliant angioplasty balloon catheter has been used to apply a radially expansive force to the ePTFE tubular graft material within the molding apparatus 100 and 130. A sintered ePTFE tubular graft was engaged into and through the common longitudinal lumen 122 of a fully assembled molding apparatus 100. An angioplasty balloon catheter was passed though the lumen of the sintered ePTFE tubular graft until the balloon was positioned within a longitudinal section of the ePTFE graft which resides in the molding cavity 120. The angioplasty balloon was inflated by applying a positive pressure to a body of water from a pressure syringe, through the catheter lumen to the angioplasty balloon. Radial expansion of the angioplasty balloon caused the balloon to impinge upon the lumenal wall of the ePTFE tubular graft, which then radially expanded by deformation of the polytetrafluoroethylene material matrix under the influence of the applied radial pressure into the molding cavity 120. After radial expansion of the ePTFE tubular graft was completed, the radially expansive fluid pressure was withdrawn, the balloon collapsed and the angioplasty balloon catheter removed from the lumen of the ePTFE tubular graft. The ePTFE tubular graft was then removed, and trimmed to form a bilateral flange as described above with reference to the preferred embodiment of the flanged distal bypass graft 10.

Alternative methods of radially expanding an ePTFE tubular graft within the molding apparatus 100 or 130 are also contemplated by the present invention. Other such alternative methods include, without limitation:

a) using a non-compliant shaped balloon where the shape of the non-compliant balloon corresponds to the shape of the molding cavity 120, 134;

b) employing an expansion mandrel having a radially expanding member coupled to the expansion mandrel;

c) using a spider member in which a section of the spider member circumferentially extends from a central rod member under the influence of an applied positive pressure and impinges upon a lumenal surface of the ePTFE graft to radially expand the ePTFE graft into the molding cavity 120, 134;

d) employing a coil spring member in which a coil spring section of a longitudinal rod member uncoils under upon torsional rotation of the longitudinal rod member and impinges upon a lumenal surface of the ePTFE graft to radially expand the ePTFE graft into the molding cavity 120, 134; or e) utilizing a mesh spring member, fixed on a distal end to a first rod member and fixed on a proximal end to a second rod member, concentric and co-axial with the first rod such that axial movement of the first rod and second rod members relative to one another longitudinally compresses or longitudinally extends the mesh spring member, causing the mesh spring member to extend radially from the first and second rod members upon a compression stroke, and return to a concentric, non-radially extended position upon an axial extension stroke.

FIGS. 14A and 14B illustrate the inventive molding apparatus 100 having an internal mold cavity 120, with an ePTFE tubular graft 142 axially positioned in the molding apparatus 100 before (FIG. 14A) and after (FIG. 14B) radial expansion within the mold cavity 120. A balloon catheter 144 having a radially expandable balloon 146, which is either a compliant balloon which substantially assumes the dimensional configuration of the mold cavity 120 upon expansion or is a non-compliant balloon to correspond to the dimensional configuration of the mold cavity 120, is axially positioned with the lumen of the ePTFE tubular graft 142 such that the balloon 146 is adjacent a longitudinal section of the ePTFE graft 142, which is resident in the mold cavity 120. Inflation of the balloon catheter 144, using a positive fluid pressure, typically provided by a syringe pump and water or saline, radially expands the balloon 146 into contact with the lumenal surface of the ePTFE tubular graft 142 and, upon application of sufficient pressure, the longitudinal section of the ePTFE tubular graft 142 resident within the mold cavity 120 is radially expanded and urged into conformation with the dimensional configuration of the mold cavity 120 as shown in FIG. 14B. It has been found that the pressure required to radially expand the longitudinal section of the ePTFE tubular graft 142 within the mold cavity 120 is dependent upon the material properties of the ePTFE tubular graft selected. The material properties of the ePTFE which govern radial expansion pressures include, without limitation, wall thickness, porosity, internodal distance, burst strength, radial tensile strength, and hoop stress. Experiments conducted using the molding apparatus 100 and an embolectomy balloon catheter have found that the applied pressures to radially expand a longitudinal section of an ePTFE tubular graft into the mold cavity 120 range from approximately 26 psi to about 100 psi at approximately 37° C. to radially expand ePTFE tubular grafts having wall thicknesses of 0.3 to 0.6 mm by between approximately 25% to about 500% the original diameter of the ePTFE tube.

The method 150 for making the flanged distal bypass graft using the inventive molding apparatus 100, 130 is described in the flowchart presented in FIG. 15. A mold with a predetermined mold cavity configuration corresponding to the taper, flange, or skirt configuration desired is provided at step 152. The mold may be a pre-assembled mold or may be assembled at step 154 from a molding tube and mold blocks as described above. An ePTFE tubular graft is then loaded onto a loading mandrel in step 156, the loading mandrel having an outer diameter which permits the selected ePTFE tubular graft to be loaded concentrically thereupon with a tight tolerance between the loading mandrel and the ePTFE graft without substantially radially expanding the graft on the loading mandrel. Alternatively, the loading mandrel may have an outer diameter which is larger than the inner diameter of the ePTFE tubular graft by up to 30% in order to pre-dilate the ePTFE tubular graft and lower the applied pressure needed to radially expand the ePTFE tubular graft into the mold cavity. Furthermore, the loading mandrel may have a tapered section which positionally corresponds to a tapered lumenal section of the molding apparatus to further facilitate radial expansion of the ePTFE tubular graft in the molding apparatus.

The loading mandrel with the ePTFE tubular graft mounted thereupon is then axially positioned in the molding apparatus in step 158 and the loading mandrel is withdrawn in step 160. A radially expansive pressure is exerted to the ePTFE tubular graft in step 162 to radially expand at least a longitudinal portion of the ePTFE tubular graft into the mold cavity of the molding apparatus in step 170. As described above, the radially expansive pressure may be an applied fluid pressure at step 164, a mechanically deforming mandrel, such as a spider, a radially expansive mesh, or the like, at step 166, or a compliant or shaped non-compliant balloon, such as an angioplasty or embolectomy balloon catheter at step 168. The radially expansive force is then released at step 172, and the molded graft is withdrawn from the mold and trimmed by cutting or other means to obtain the desired shape of flange or skirt at step 174.

While the foregoing is a description of the broad method steps of the inventive method 150, it is believed within the ordinary skill of one in the art to define the particular mold configuration, the means for exerting a radially expansive pressure to the ePTFE tubular graft, the desired material properties of the ePTFE tubular graft, and temperatures and pressures under which the method is executed. Thus, while the present invention has been disclosed and described with reference to its preferred embodiments, those skilled in the art will understand and appreciate that modifications in material selection, dimension, and construction may be made without departing from the scope of the present invention, which is limited only by the claims appended hereto.

What is claimed is:

1. A method for making a vascular graft, comprising the steps of:

radially expanding at least a longitudinal section of a tubular graft member formed of microporous expanded polytetrafluoroethylene in a mold cavity to an expanded diameter which is greater than remaining radially unexpanded longitudinal sections of the expanded polytetrafluoroethylene tubular graft member, where a tapered longitudinal section is interdisposed between the radially expanded and radially unexpanded longitudinal sections of the expanded polytetrafluoroethylene tubular graft member;

removing the expanded polytetrafluoroethylene tubular graft member from the mold cavity; and trimming the expanded polytetrafluoroethylene tubular graft member to form a vascular graft having at least one flanged section or a collar section projecting from a distal end thereof.

2. The method of claim 1, wherein the step of trimming comprises forming at least one flanged section which projects outwardly away from a central axis of the tubular graft member at the distal end thereof, the at least one flanged section being a continuous and integral section of the expanded polytetrafluoroethylene tubular graft member.

3. The method of claim 2, wherein the step of trimming further comprises a step of forming a collar section circumferentially extending about an entire circumferential aspect of a distal end of the radially expanded longitudinal section of the expanded polytetrafluoroethylene tubular graft member.

4. The method of claim 2, wherein the step of trimming further comprises forming a collar section as an elliptical shape having foci offset with respect to a central longitudinal axis of the expanded polytetrafluoroethylene tubular graft member and angularly displaced such that a greater aspect of the elliptical shape projects distally and a smaller aspect of the elliptical shape projects proximally relative to the longitudinal axis of the expanded polytetrafluoroethylene tubular graft member.

5. The method of claim 1, wherein the step of trimming comprises forming at least one flanged section projecting radially outwardly away from a central axis of the tubular graft member.

6. The method of claim 5, wherein the step of trimming comprises forming at least one flanged section, and the step of forming at least one flanged section further comprises the step of forming two flange sections projecting radially outward from the central axis of the tubular graft member and in opposing directions relative to one another.

7. The method of claim 6, wherein the two flange sections as substantially symmetrical mirror-images of one another.

8. The method of claim 6, wherein the two flange sections as substantially asymmetrical to one another.

9. The method of claim 1, wherein the step of trimming comprises forming a collar section circumferentially extending about an entire circumferential aspect of the distal end of the radially expanded longitudinal section of the expanded polytetrafluoroethylene tubular graft member.

10. The method of claim 9, wherein the collar section is formed as an elliptical shape having foci offset with respect to a central longitudinal axis of the expanded polytetrafluoroethylene tubular graft member and angularly displaced such that a greater aspect of the elliptical shape projects distally and a smaller aspect of the elliptical shape projects proximally relative to the longitudinal axis of the expanded polytetrafluoroethylene tubular graft member.

11. The method of claim 10, wherein the step of forming the collar section further comprises forming a toe section and a heel section, the toe section comprising the greater aspect of the elliptical shape and the heel section comprising the smaller aspect of the elliptical shape.

12. The method of claim 11, wherein the step of forming the collar section further comprises the step of molding the toe section such that it is angularly displaced between 95° to 160° relative to a central longitudinal axis of the expanded polytetrafluoroethylene tubular graft member.

13. The method of claim 12, wherein the step of forming the collar section further comprises the step of molding the heel section such that it is angularly displaced between 20° to 85° relative to the central longitudinal axis of the expanded polytetrafluoroethylene tubular graft member.

14. The method of claim 13, wherein the step of forming the collar section further comprises the step of trimming an arcuate outer peripheral edge which subtends an arc of 180° arc and forms a continuous surface interconnecting the toe section and the heel section.

15. An apparatus for making a flanged vascular graft, comprising:
   a molding tube member having first and second open ends;
   a first tubular mold block member having a central longitudinally oriented lumen and a mold face, the first tubular mold block being engageable within the molding tube member at the first open end thereof,
   a second tubular mold block member having a central longitudinally oriented lumen and a mold face, the second tubular mold block being engageable within the molding tube member at the second open end thereof,
   a common lumen defined by the each of the central longitudinally oriented lumens of the first and second tubular mold block members which are co-axially aligned relative to one another, the common lumen communicating between the first and second open ends of the molding tube member;
   a mold cavity defined by the mold faces of each of the first and second tubular mold block members and a circumferential section of the molding tube member; and
   means for retaining the first and second mold block members in a fixed position within the molding tube member comprising a plurality of apertures passing through each of the molding tube member, the first mold block member and the second mold block member, wherein said plurality of apertures are capable of variable alignment with one another, and a plurality of lock pin members engageable through the plurality of apertures.

16. The apparatus of claim 15, wherein at least one of the lumen of the first mold block member and the lumen of the second block member further includes a tapered section transitioning between a larger lumenal diameter and a smaller lumenal diameter section of the lumen.

17. The apparatus of claim 15, wherein at least one of the lumen of the first mold block member and the lumen of the second block member further includes a tapered section transitioning between a larger lumenal diameter and a smaller lumenal diameter section of the lumen.

18. The apparatus of claim 15, wherein the means for retaining the first and second mold block members further comprises an adhesive.

19. The apparatus of claim 18, wherein at least one of the lumen of the first mold block member and the lumen of the second block member further includes a tapered section transitioning between a larger lumenal diameter and a smaller lumenal diameter section of the lumen.

* * * * *

UNITED STATES PATENT AND TRADEMARK OFFICE
CERTIFICATE OF CORRECTION

PATENT NO. : 6,190,590 B1  
DATED : February 20, 2001  
INVENTOR(S) : Scott Randall, Roy H. Tang and Albert L. Lamay It is certified that error appears in the above-identified patent and that said Letters Patent is hereby corrected as shown below:

Column 17,  
Line 21, change "as" to -- are --.  
Line 23, change "as" to -- are --.

Signed and Sealed this

Eleventh Day of June, 2002

Attest:

JAMES E. ROGAN  
Attesting Officer     Director of the United States Patent and Trademark Office

UNITED STATES PATENT AND TRADEMARK OFFICE
CERTIFICATE OF CORRECTION

PATENT NO. : 6,190,590 B1
DATED : February 20, 2001
INVENTOR(S) : Scott L. Randall et al.

It is certified that error appears in the above-identified patent and that said Letters Patent is hereby corrected as shown below:

Delete Drawing sheets 1 of 4, and 2 of 4, and substitute therefore the drawing sheets attached.

Column 5,
Line 1, "2" should be changed to -- 10 --.

Column 6,
Lines 7 and 10, "8" should be deleted.
Line 24, "8" should be changed to -- 9 --.
Line 29, "8" in both occurrences should be changed to -- 9 --.

Signed and Sealed this

Thirteenth Day of September, 2005

JON W. DUDAS
*Director of the United States Patent and Trademark Office*